United States Patent [19]

Jaeger et al.

[11] 4,026,942
[45] May 31, 1977

[54] THERAPEUTICALLY EFFECTIVE N-SUBSTITUTED UREAS

[75] Inventors: Karl-Heinz Jaeger, Obereggenen; Hermann Kasparek, Oberkirch, Baden, both of Germany; Willy Herbrand, deceased, late of Gengenbach, Baden, Germany, by Elisabeth Herbrand nee Lauterbach, heir

[73] Assignee: Solco Basel AG, Gengenbach, Baden, Germany

[22] Filed: Aug. 25, 1975

[21] Appl. No.: 607,689

Related U.S. Application Data

[60] Continuation of Ser. No. 391,016, Aug. 23, 1973, abandoned, which is a division of Ser. No. 109,990, Jan. 26, 1971, abandoned.

[52] U.S. Cl. .................... 260/553 R; 424/322
[51] Int. Cl.² ............... C07C 127/15; A61K 31/17
[58] Field of Search ............... 260/553 R; 424/322

[56] References Cited

UNITED STATES PATENTS

| 2,163,043 | 6/1939 | Ktitchevsky | 260/553 R X |
| 2,230,082 | 1/1941 | Montenier | 260/553 R X |

FOREIGN PATENTS OR APPLICATIONS

| 1,242,591 | 6/1967 | Germany |
| 1,908,047 | 9/1970 | Germany |

OTHER PUBLICATIONS

CA 67:89835e (1967).
Kerp, Justuo Liebigs Annalen der Chemie, vol. 290, pp. 135, 136, 150 & 151, (1896).

*Primary Examiner*—Daniel E. Wyman
*Assistant Examiner*—Thomas A. Waltz
*Attorney, Agent, or Firm*—Flynn & Frishauf

[57] ABSTRACT

N-mono-substituted ureas represented by

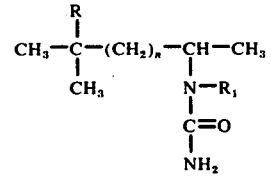

wherein R is hydrogen, hydroxyl, or thiol, $R_1$ is hydrogen, methyl or ethyl and n is 1, 2, 3 or 4, have therapeutic properties.

3 Claims, No Drawings

THERAPEUTICALLY EFFECTIVE N-SUBSTITUTED UREAS

This is a continuation, of application Ser. No. 391,016, filed Aug. 23, 1973, which, in turn, is a division of application Ser. No. 109,990, filed Jan. 26, 1971. Each of said applications has been abandoned.

The present invention relates to novel therapeutically effective N-substituted ureas.

The therapeutically active compounds are represented by the general formula

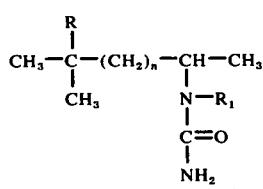

in which

R is hydrogen or a hydroxyl or thiol group, $R_1$ is hydrogen or a lower alkyl group ($C_{1-2}$), and n is a whole number between 1 and 4.

It is known that lower aliphatic amines have sympathikomimetic properties, which for example, cause an increase in blood pressure. This pressure increasing effect seems to have its basis less in toning of the vascular system; rather, it appears that it is based essentially on improvement of heart action, similar in effect to strophanthin. In general, the effective period of these substances is relatively short, so that frequent application is necessary to obtain an adequate therapeutic effect.

We have found that by converting the therapeutically active primary or secondary amines into urea derivatives, compounds having increased tonic effect upon the heart are obtained.

The effective period of the urea compounds is substantially increased with respect to that of the amines. The new compounds are further characterized by very good tolerance by humans.

Preparation of the substituted urea compounds is preferably made by reacting suitable primary or secondary amines with cyanic acid, as indicated below:

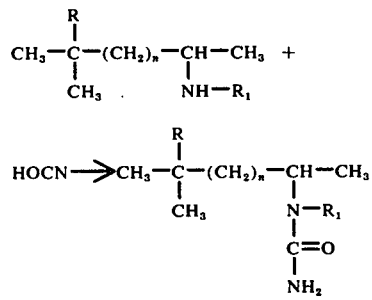

Hydrochlorides of the amines are suitably heated with an alkali metal or alkaline earth metal salt of cyanic acid in an aqueous solution to a temperature between about 50° C. and about 90° C. The reaction product is first separated as an oil, which crystallizes upon cooling.

EXAMPLES

1. Preparation of N—6-methyl-heptyl(2)—urea.

16.6 grams (0.1M) of 6-methyl-2-amino-heptane hydrochloride dissolved in 50 ml of water are heated to 75° C. in a 250 ml 3-neck flask fitted with a stirrer, a dropping funnel, and a thermometer. According to the general formula, R and $R_1$ are hydrogen and n is 3. Under vigorous stirring, a solution of 8.5 g (0.105 M) of potassium cyanate in 20 ml water is added to the flask. After the addition has terminated, the reaction product separates in the form of colorless, scaly crystal. Heating is continued for 1 hour, and the resulting mixture is cooled to 20° C. The crystallized product is separated from the reaction product by suction and is washed with demineralized water until no chloride is present in the wash water. Thereafter, the crystals are dried at 80° C. in a drying oven. The product is dissolved in 350 ml of boiling ethyl acetate and filtered rapidly. The reaction product is separated in the form of colorless platelets.

The yield of desired product is 17 grams (99% of theoretical). The melting point is 141°–142° C.

2. Preparation of N—6-Methyl-6-hydroxy-heptyl(2)—urea 127 grams (0.7 M) of 6-methyl-6-hydroxyl-2-amino-heptane hydrochloride dissolved in 50 ml of water are heated to 70°–75° C. in a 500 ml flask as described in Example 1. In this compound, R is hydroxyl, $R_1$ is hydrogen and n is 3. Under vigorous stirring and within a few minutes, a solution of 58.4 g (0.721 M) of potassium cyanate in 70 ml water is added to the flask. The reaction mixture is heated for 3 hours for 70°–75° C. and stirred vigorously. During this time, a colorless oil separates. After the reaction has terminated, the hot reaction product is poured into a beaker and stirred while simultaneously cooling the outside with ice water, until crystallization occurs, and the mixture is cooled to 10° C. By sharp suction or, better centrifuging, as much as possible of the crystals are separated from the resulting mass. Thereafter, the product is dried at 70° C. in a vacuum drier chamber until the weight is constant. The mass is finely pulverized and is heated for 20 minutes in 700 ml of boiling ethyl acetate. It is removed by suction rapidly from the undissolved potassium chloride. Reaction product is separated in the form of colorless small crystals from the filtrate upon cooling.

The yield is 129 grams (98% of theoretical). Melting point is 107°–109° C.

3. Preparation of N—6-Methyl-6-mercapto-heptyl(2)—urea

In a 500 ml multineck flask fitted with a stirrer, thermometer, dropping funnel, and a gas inlet tube, nitrogen is introduced into 64.4 g (0.4 M) of 6-methyl-6-mercapto-2-amino-heptane. In this compound, R is thiol, $R_1$ is hydrogen and n is 3. With stirring and exterior water cooling, a 12% aqueous hydrochloric acid is dripped into the flask until the resulting liquid has a pH of 3. The temperature should not exceed 20° C. Thereafter, 150 ml water are added, followed by a solution of 34 g (0.42 M) of potassium cyanate in 70 ml of water. The resulting mixture is heated, under stirring, in a nitrogen atmosphere to 65°–75° C. for 1 hour. Shortly, after reaching this temperature, a fine-crystalline precipitate separates. After the reaction is terminated, the mixture is cooled to 10° C., and the crystal mass is filtered. A colorless cyrstalline product is obtained and is washed with water and recrystallized from aqueous ethanol (1:1). The reaction product precipitates in the form of colorless small crystals.

The yield of desired product is 76 grams (93% of theoretical). The melting point is 134°–136° C.

The above described examples relate to heptyl compounds, in which $n$ is 3. Homologs of the substituted urea products having suitably changed starting components, that is $n$ equal to 1, 2 or 4, in accordance with test data, also have advantageous and novel pharmaceutical properties.

The Methyl-heptyl-carbamide has, compared with other penetration stimulators, a considerably stronger effect on the deadly poisoned (Nembutal) heart of the cat in situ. The blood pressure decreased to 0 is nearly immediately raised to the starting level, which could never be observed before with another substance; respiration and frequency of the heart are restored spontaneously.

The use of the new compounds is justified by their stronger, quicker and longer-lasting effect on heart, circulation and respiration, with substantially the same dosage as previously known penetration stimulators.

We claim:

1. A substituted urea having the formula

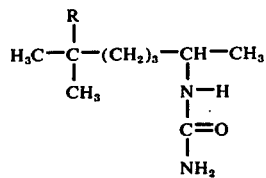

wherein R is hydrogen or a hydroxyl group.

2. N—6-Methyl-heptyl (2)—urea of the formula of claim 1.

3. N—6-Methyl-6-hydroxy-heptyl (2)—urea of the formula of claim 1.

* * * * *